United States Patent [19]

van Lintel

[11] Patent Number: 5,085,562
[45] Date of Patent: Feb. 4, 1992

[54] MICROPUMP HAVING A CONSTANT OUTPUT

[75] Inventor: Harald van Lintel, Martigny, Switzerland

[73] Assignee: Westonbridge International Limited, Dublin, Ireland

[21] Appl. No.: 503,977

[22] Filed: Apr. 4, 1990

[30] Foreign Application Priority Data

Apr. 11, 1989 [CH] Switzerland ................ 01369/89

[51] Int. Cl.⁵ .............................................. F04B 35/04
[52] U.S. Cl. .................... 417/413; 417/412; 417/322
[58] Field of Search .................... 417/322, 412, 413

[56] References Cited

U.S. PATENT DOCUMENTS

| | | | |
|---|---|---|---|
| 3,150,592 | 9/1964 | Stec | 417/322 |
| 3,215,078 | 11/1965 | Stec | 417/322 |
| 4,265,600 | 5/1981 | Mandroian | 417/379 |
| 4,265,601 | 5/1981 | Mandroian | 417/379 |
| 4,708,600 | 11/1987 | AbuJudom, II et al. | 417/322 |
| 4,911,616 | 3/1990 | Laumann, Jr. | 417/413 |
| 4,938,742 | 7/1990 | Smits | 417/322 X |

FOREIGN PATENT DOCUMENTS

| | | |
|---|---|---|
| 134614 | 3/1985 | European Pat. Off. . |
| 2639992 | 3/1978 | Fed. Rep. of Germany . |
| 2127774 | 10/1972 | France . |
| 0171891 | 8/1986 | Japan ...................... 417/322 |
| 2077367 | 12/1981 | United Kingdom . |

OTHER PUBLICATIONS

Article entitled "Sensors and Actuators" by Harald van Lintel, vol. 15, No. 2, pp. 154–167, dated Oct. 2, 1988.

Primary Examiner—John Rivell
Attorney, Agent, or Firm—Pollock, Vande Sande & Priddy

[57] ABSTRACT

A micropump comprising a pumping chamber, an inlet channel communicating with the pumping chamber by an inlet valve and an outlet channel communicating with the pumping chamber via an outlet valve, these elements being manufactured by etching a silicon wafer is then sealed to glass wafers, the micropump also comprising a piezoelectric wafer to vary the volume of the pumping chamber by bending a wall forming part of the wall of this pumping chamber. In accordance with the invention the pumping chamber has a stop which determines the amplitude of movement of the flexible wall. The variation in the volume of the chamber caused by the displacement of the flexible wall is precisely defined, thus making it possible to maintain the output of the micropump constant during normal operating conditions.

21 Claims, 4 Drawing Sheets

MICROPUMP HAVING A CONSTANT OUTPUT

TECHNICAL FIELD

The present invention relates to a micropump in which at least part of the pump mechanism is made by machining a silicon wafer using photolithographic technology.

BACKGROUND OF THE INVENTION

Micropumps can be used in particular for the in situ administration of medicaments, the miniaturization of the pump making it possible to implant them permanently in the body. Using these pumps, small quantities of liquid to be injected can be accurately metered.

Micropumps of this type are in particular described in the article "A piezoelectric micropump based on micromachining of silicon" by H. van Lintel et al. which appeared in Sensors and Actuators, No. 15, 1988, pages 153-157. These micropumps substantially comprise a stack of three wafers, i.e. a wafer of silicon arranged between two wafers of glass.

The wafer of silicon is etched to form a cavity which, together with one of the glass wafers, defines the pumping chamber, at least one inlet valve and at least one outlet valve enabling the pumping chamber to communicate with one inlet channel and one outlet channel respectively. The part of the glass wafer forming a wall of the pumping chamber can be bent by a control element composed, for example, of a piezoelectric disc. This is provided with two electrodes which, when connected to a source of electrical potential, cause the disc to bend and, consequently, bend the glass wafer, causing a variation in the volume of the pumping chamber. The flexible wall of the pumping chamber can therefore be displaced between a first position, in which it is relatively far from the opposing wall when the piezoelectric disc is not subjected to any electrical potential, and a second position in which it is closer to the opposite wall when a potential is applied between the electrodes of the piezoelectric disc.

The micropump operates in the following manner. When no electrical potential is applied to the piezoelectric disc, the inlet and outlet valves are in the closed position. When an electrical potential is applied, the pressure inside the pumping chamber increases, causing the outlet valve to open as soon as the pressure in the chamber is greater than the sum of the pressure in the outlet channel and the pressure created by the pre-tension of the valve. The fluid contained in the pumping chamber is then forced towards the outlet channel by the displacement of the flexible wall from the first position towards the second position. During this phase the inlet valve is kept closed by the pressure prevailing in the pumping chamber.

In contrast, the pressure in the pumping chamber falls when the electrical potential is reduced. This closes the outlet valve as soon as the pressure in the pumping chamber is lower than the sum of the pressure in the outlet channel and the pressure created by the pre-tension of the valve, and opens the inlet valve as soon as the sum of the pressure in the pumping chamber and the pressure created by the pre-tension of the valve is less than the pressure in the inlet channel. Fluid is then sucked into the pumping chamber via the inlet channel as a result of the displacement of the flexible wall from the second position towards the first position.

As has already been stated, these micropumps are used in particular for the administration of medicaments. It is therefore important for the output of the micropump to be well determined so that the medication to be injected can be metered in a very precise manner. However, conventional micropumps have certain defects in this respect.

The output of the micropump depends on the variation in the volume of the pumping chamber between the two positions of the flexible wall. This variation in volume depends on various parameters, including the electrical potential applied to the piezoelectric disc and the physical characteristics of the piezoelectric disc (thickness, diameter, dielectric constant) and of the flexible wall (material, thickness). The same electrical potential applied to seemingly identical micropumps could cause differing bending of the pumping chambers of these micropumps which would consequently have different outputs.

The output from one and the same micropump could, moreover, also change in the course of time due to ageing of the materials. Finally, the output of the micropump depends on the pressure in the outlet channel, since the outlet valve only opens when the pressure in the pumping chamber is greater than the sum of the pressure in the outlet channel and the pressure created by the pre-tension of the valve.

In the above mentioned article, H. van Lintel et al. describe a micropump provided with an additional valve which makes it possible to render the output less dependent on the pressure in the outlet channel. However, this micropump does not overcome the other disadvantages mentioned earlier.

SUMMARY OF THE INVENTION

It is the main object of the invention to overcome the above-mentioned disadvantages in order to ensure that the output of the micropump is as constant as possible and, in particular, independent of the manufacturing tolerances of the micropump, of the ageing thereof and of the pressure in the outlet channel.

The micropump of the invention comprises a plurality of wafers bonded to one another in a sealed manner in which are formed a pumping chamber defined by two bonded wafers defining a cavity obtained by etching at least one of these wafers, at least one inlet valve and at least one outlet valve enabling the pumping chamber to communicate with one inlet channel and one outlet channel respectively, this micropump comprising in addition a control element for resiliently bending the part of a wafer constituting one wall of the pumping chamber between a first position in which this bent wall is further from the opposing wall of the pumping chamber and a second position in which this wall is relatively close to this opposing wall, the displacements of the flexible wall causing the suction or delivery of a fluid. According to the invention, this micropump is characterized in that the pumping chamber has a stop which determines the second position of the flexible wall.

This stop limits the movement of the flexible wall towards the opposing wall of the pumping chamber. This makes it possible to define the volume of the pumping chamber in a very precise manner at the end of the fluid delivery operation.

In addition, the presence of this stop means that it is no longer necessary for the electrical control potential of the piezoelectric disc, or more generally, the intensity of the signal applied to the bending control unit of the flexible wall, to have a precise value. It suffices if this potential is greater than that needed to effect a contact between the stop and the opposing wall of the pumping chamber.

Finally, the stop permits an output substantially independent of the pressure prevailing in the outlet channel since it is possible to impart a high potential to the piezoelectric disc, inducing a high pressure in the pumping chamber which is higher than the sum of the pressure prevailing in the outlet channel in normal conditions of use and the pressure created by the pre-tension of the outlet valve, without this latter being altered by an increase in the amplitude of movement of the flexible wall which remains fixed by the stop.

This stop can in particular take the form of one or several projections which can be formed on the bottom of the cavity during the etching of the wafer in which this cavity is effected and/or provided by etching, bonding or the like on the flexible wall. The stop can also be simply composed of the bottom of the cavity itself provided the height of the pumping chamber is selected so that it is equal to the desired amplitude of the movement of the flexible wall.

BRIEF DESCRIPTION OF THE DRAWINGS

The characteristics and advantages of the invention are better illustrated by the following description, given for purposes of example and which is not limiting, with reference to the accompanying drawings, in which.

DETAILED DESCRIPTION

Figure 1A:
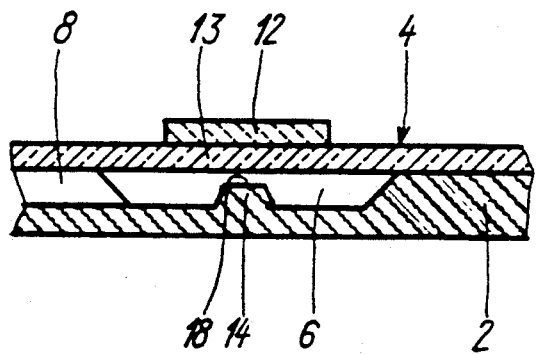
FIG. 1A shows a section along the line I—I of a pumping chamber of a micropump according to the invention in which the flexible wall is shown in the first position.

A first embodiment of a pumping chamber for a micropump according to the invention will be described with reference to FIGS. 1A, 1B, and 2. This pumping chamber is determined by the wafers 2, 4 sealed to each other, for example by anodic welding or by adhesion. These wafers are generally of the order of a few tenths of a millimeter thick. The cavity 6 defining the pumping chamber as well as an inlet channel 8 and an outlet channel 10 are obtained by etching the wafer 2 using conventional photolithographic techniques, such as wet etching. The diameter of the cavity is of the order of 1 cm and it is between 5 and 200 micrometers high. The wafer 2 is of a material which can be easily etched, such as monocrystalline silicon; the wafer 4 is for example of glass.

A control element such as, for example, a piezoelectric disc 12 is bonded to the outside face of the wafer 4 at the level of the cavity 6. Each face of this piezoelectric disc is covered by an electrode connected to a source of potential (not shown).

Figure 2:
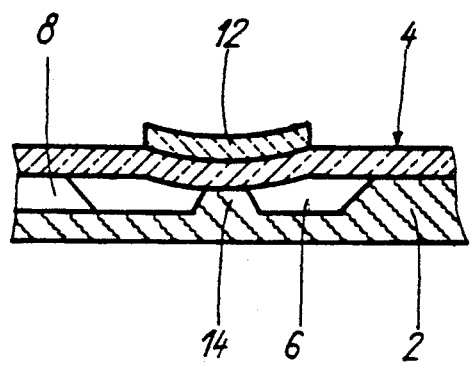
FIG. 2 shows a section along the line I—I of the pumping chamber of FIGS. 1A and AB in which the flexible wall is in the second position, FIGS. 3A and 3B respectively show a section along the line III—III and a plan view of an embodiment of a pumping chamber for a micropump according to the invention.

FIGS. 1A and 2 respectively illustrate the position of the wafer 4 in which no electrical potential is applied to the piezoelectric disc 12 (first position) or in which an electrical potential is applied to this piezoelectric disc (second position).

According to the invention the pumping chamber is provided with a stop 14 which, in limiting the amplitude of the movement of the flexible wall 13 of the wafer 4, precisely defines the second position of this flexible wall. As a result, the volume of the pumping chamber at the end of the delivery operation, i.e. when the flexible wall 13 is in the second position, has a value that is precisely definable and reproducible.

Figure 3A:
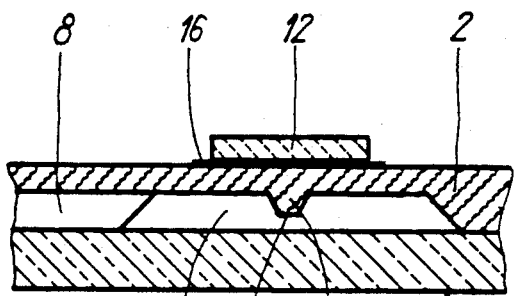
Figure 3B:
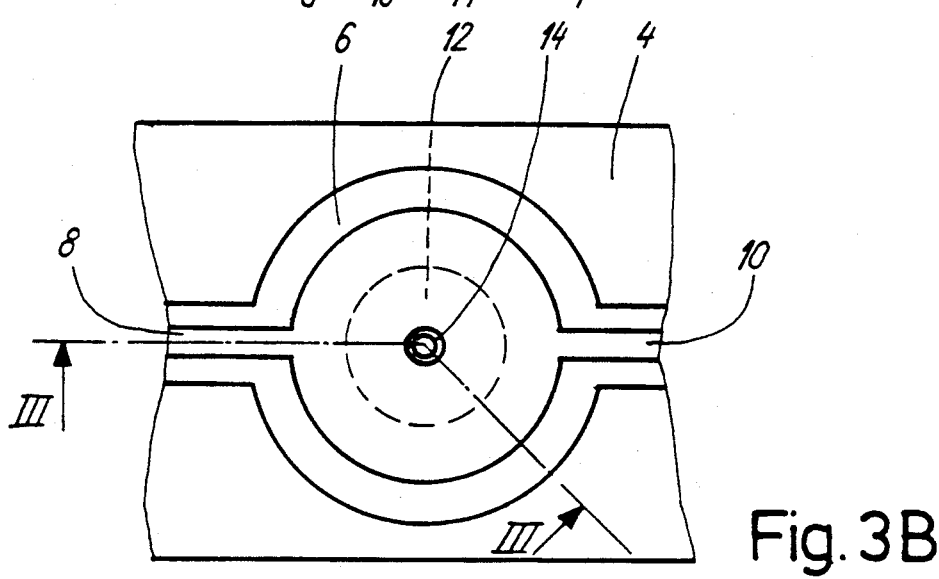

When the flexible wall is in the first position the distance between the stop and the opposing wall of the chamber is of the order of 10 μm or less. This distance clearly depends on the dimensions of the pumping chamber and on the fluid output desired In the embodiment shown in FIGS. 1A, 1B and 2, the piezoelectric disc 12 is fixed to the glass wafer 4. It is of course possible to fix the piezoelectric disc 12 onto the silicon wafer 2. A pumping chamber of this type is shown in section along the line III—III and in plan view in FIGS. 3A and 3B respectively.

Figure 1B:
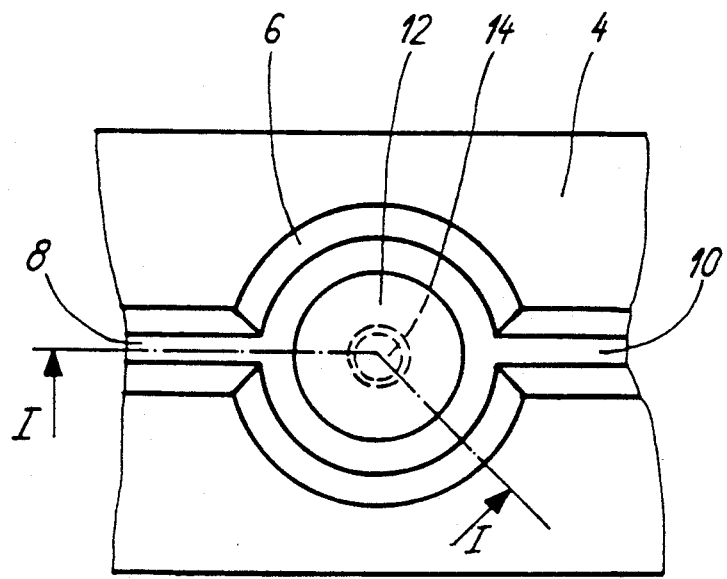
FIG. 1B shows a plan view of the pumping chamber shown in FIG. 1A.

In these figures the elements identical to those shown in FIGS. 1A, 1B and 2 have the same reference numerals. When the silicon wafer 2 supports the piezoelectric disc 12, a layer 16 of $SiO_2$ is interposed between the disc 2 and the piezoelectric disc 12 for purposes of electrical insulation. Finally, it should be noted that, in this embodiment, the diameter of the stop 14 must be substantially lower than that of the piezoelectric disc so as not to excessively restrict the flexibility of the wafer 2.

In the two first described embodiments, the stop 14 is composed of a stop which extends from one wall of the pumping chamber. This projection is provided in the silicon wafer 2 during the etching of the cavity and of the inlet and outlet channels The upper surface 18 of the projection, against which the opposing wall of the pumping chamber impinges when the piezoelectric disc is subjected to an electrical potential is preferably planar. This makes it possible to define the second position of the flexible wall more precisely.

Figure 4:
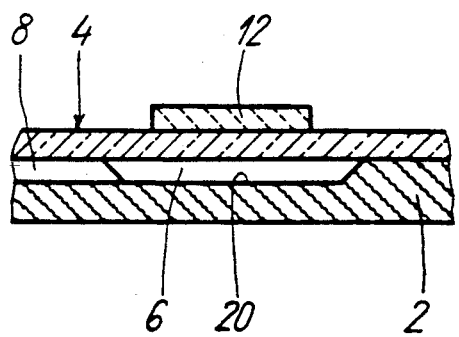
FIG. 4 is a transverse section of another embodiment of a pumping chamber for a micropump according to the invention in which the flexible wall is in the first position.
Figure 5:
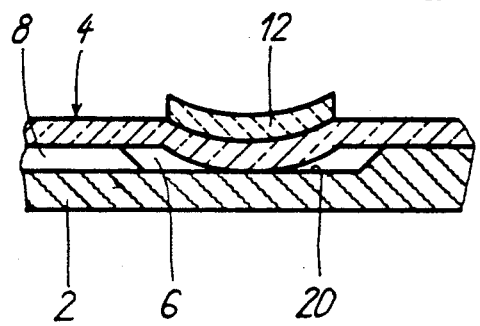
FIG. 5 shows, in transverse section, the pumping chamber of FIG. 4 in which the flexible wall is in the second position, FIGS. 6A and 6B respectively show a section along the line VI—VI and a plan view of a micropump of the invention, FIGS. 7A and 7B respectively show a section along the line VII—VII and a plan view of another micropump of the invention.

It is also possible to use the bottom of the cavity itself as the stop. This is the case when a cavity is provided, the height of which is equal to the desired amplitude of movement of the flexible wall. FIGS. 4 and 5 show transverse sections through a pumping chamber of this kind in the first and second positions respectively of the flexible wafer 4. In these figures, the pumping chamber is defined by a cavity 6 linked to an inlet channel 8 and an outlet channel (not shown). This pumping chamber is composed of a silicon wafer 2 and a glass wafer 4 as in the previous figures. The piezoelectric disc is disposed on the glass wafer 4; this wafer 12 may of course also be disposed on the silicon disc 2, as in FIGS. 3A and 3B.

The advantage of using the bottom 20 of the cavity 6 as a stop for the flexible wall is that it reduces the number of operations needed to etch the silicon wafer 2 in comparison to the previous embodiments in which the stop is composed of a projection. Moreover, as shown in FIG. 5, the volume of the chamber at the end of the delivery phase is very small. This ensures effective pumping, even if the liquid contains many gas bubbles (provided the parasite volume between the valves and the chamber itself is also very small). On the other hand, if the volume of the pumping chamber remains relatively large at the end of the delivery phase, and this is generally the case when the stop is a projection, the gas bubbles can be compressed without being expelled from the pumping chamber.

In contradistinction it should be noted that the resistance to fluid flow is greater with a pumping chamber as shown in FIG. 4 which is thus particularly suitable for very low output micropumps.

Figure 6A:
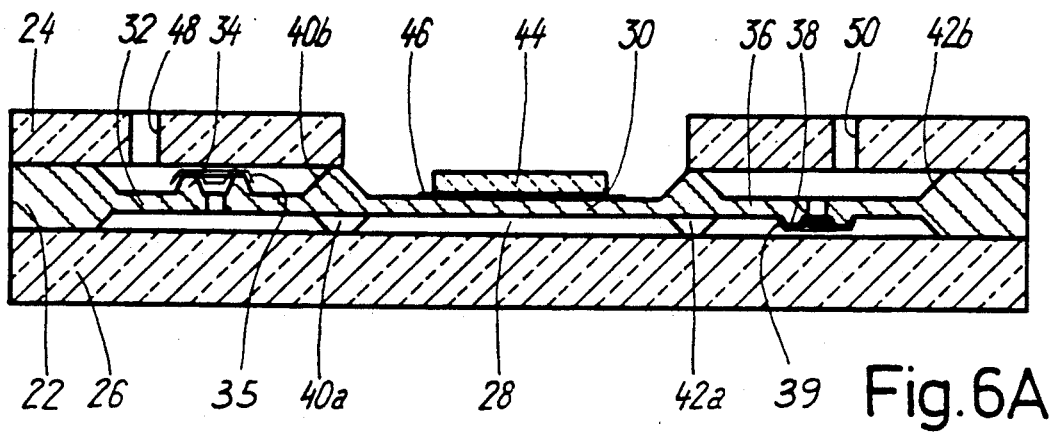
Figure 6B:
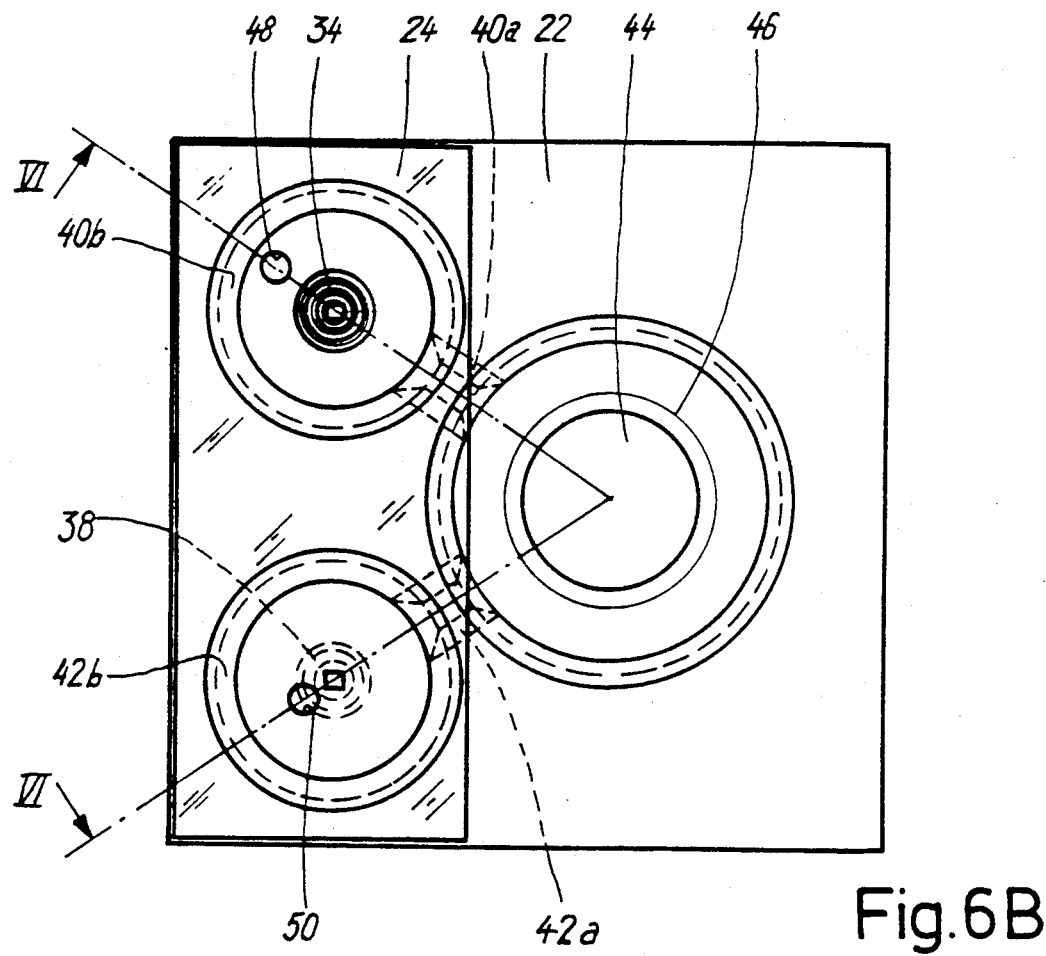

One embodiment of a micropump of the invention is shown in section along the line VI—VI and in plan view in FIGS. 6A and 6B respectively. This micropump mainly comprises a silicon wafer 22 disposed between glass wafers 24 and 26. The wafer 22 is etched on one face to form a cavity 28 defining the pumping chamber and on the other face to regulate the thickness of the part of the wafer 22 which constitutes the flexible wall 30 of the pumping chamber. This thickness is for example 150 μm.

The two faces of the wafer 22 are in addition engraved to form a membrane 32 and an annular rib 34 of an inlet valve, a membrane 36 and an annular rib 38 of an outlet valve, and an inlet channel 40a, 40b and an outlet channel 42a, 42b. To prevent the valves adhering to the glass wafers, the former are covered with a fine layer 35, 39 of SiO₂.

The piezoelectric disc 44 which controls the movement of the flexible wall 30 is bonded using cyano acrylate glue after the flexible wall has been covered with a fine layer 46 of SiO₂ to provide electrical insulation. The piezoelectric disc 44 can be of the PXE-5 type, manufactured by Philips, 10 mm in diameter and 0.20 mm thick.

Since the flexible wall 30 and the membranes 32, 36 are formed in the silicon wafer 22, the latter is preferably a wafer of monocrystalline silicon of <100> orientation with good mechanical properties and which is very suitable for etching. This disc can be 5 cm in diameter and be of the order of 300 micrometers thick.

The wafers 24 and 26 are of polished glass. They are 5 cm in diameter and 1 mm thick. The wafer 24 is pierced by an inlet hole 48 and an outlet hole 50. The wafers 24 and 26 are sealed to the wafer 22 using the technique known as anodic welding.

In the embodiment shown in FIGS. 6A and 6B, the height of the pumping chamber, that is the distance between the flexible wall 30 and the wafer 26 when no electrical potential is applied to the piezoelectric disc 44, is selected (during etching of the wafer 22) so that the stop is formed by the surface of the wafer 26. The pumping chamber is thus similar to that described with reference to FIGS. 4 and 5, the only difference being that the piezoelectric disc is fixed onto the silicon wafer instead of onto the glass wafer.

Figure 7A:
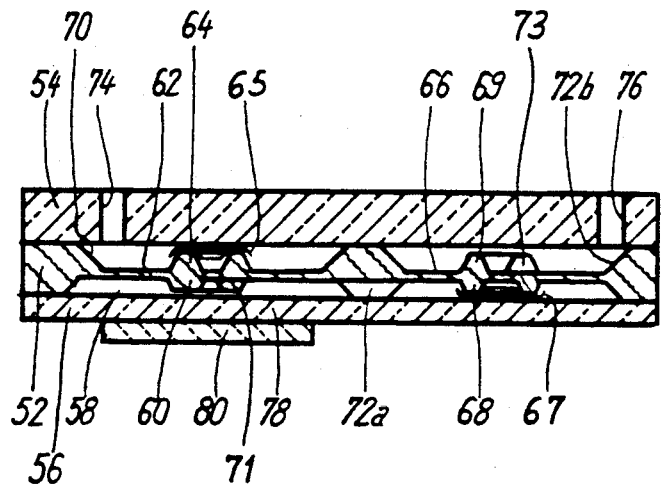
Figure 7B:
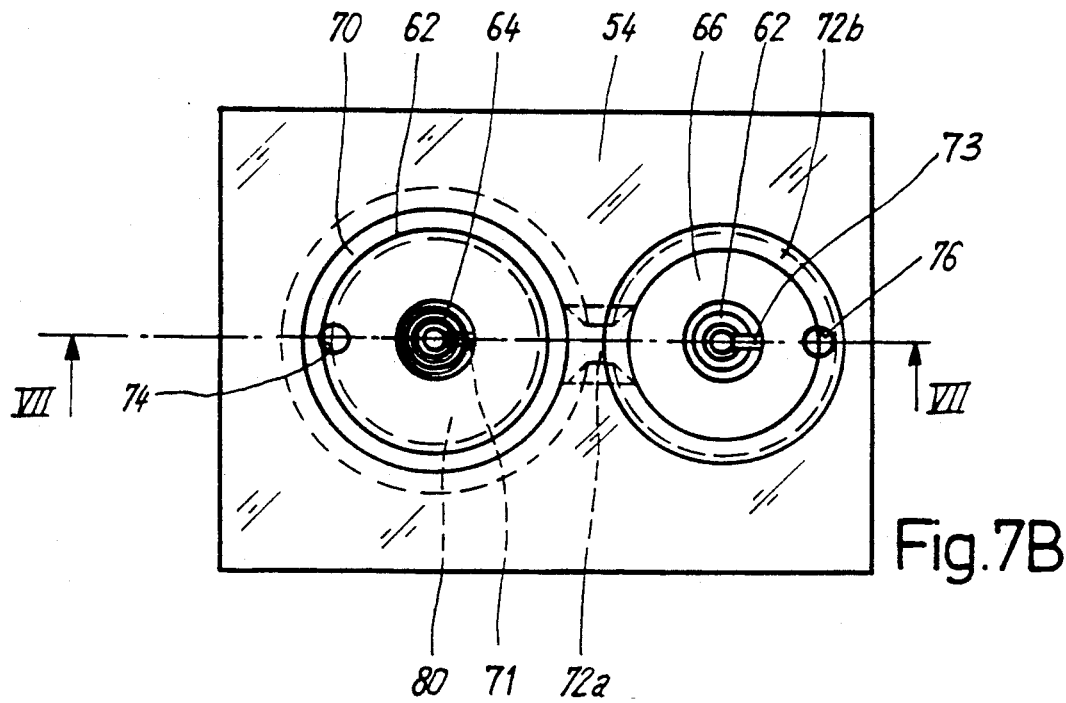

FIGS. 7A and 7B respectively show a section along the line VII—VII and a plan view of a micropump according to another embodiment of the invention. This micropump is more compact than the micropump shown in FIGS. 6A and 6B. This is achieved by placing the inlet valve of the micropump directly onto one of the walls of the pumping chamber. It would be possible also to place a part of the outlet valve thereon.

This micropump is composed of a silicon wafer 52 disposed between two glass wafers 54 and 56. One face of the wafer 52 is etched to form a cavity 58, defining the pumping chamber and during this etching operation a projection 60 is formed to constitute a stop according to the invention. The two faces of the silicon wafer 52 are also etched to form a membrane 62 and an annular rib 64 of an inlet valve, and an inlet channel 70 and an outlet channel 72a, 72b. Layers 65, 67 of SiO₂ are formed on the annular ribs 64, 68 to prevent the valves adhering to the glass wafers.

The inlet valve is preferably centered on the cavity 58. In this case, the projection 60, also centered in relation to the cavity 58 and to the inlet valve, is in the form of a ring. The valves can be provided with an amplitude limiter to reduce the risk of breakage of the membrane. In the case of the outlet valve, this limiter is composed of an annular rib 69; in the case of the inlet valve, it is the projection 60 which acts as the limiter. Channels 71, 73 are preferably provided in the amplitude limiters of the valves to permit flow of liquid when these limiters are in contact with the glass wafers 54, 56.

After the etching operations, the glass wafers 54 and 56 are sealed by anodic welding to the silicon wafer 52, the glass wafer 54 being provided with an inlet opening 74 and an outlet opening 76. The flexible wall 78 of the pumping chamber is composed of part of the glass wafer 56; its thickness is of the order of 200 μm.

A piezoelectric disc 80 is bonded to this wall 78 to control its movement. In accordance with the invention the annular projection 60 limits the amplitude of movement of the flexible wall which makes it possible to precisely define the volume of the pumping chamber at the end of the delivery operation.

Figure 8:
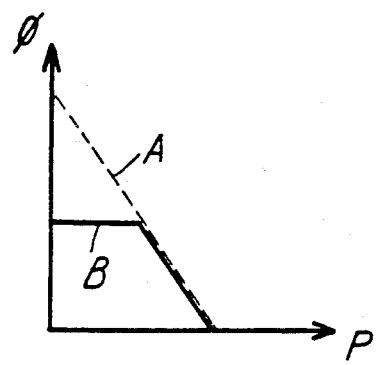
FIG. 8 is a diagram illustrating the output of a micropump as a function of the pressure in the outlet channel for a micropump having two valves of conventional type for a micropump according to the invention.

This stop also makes it possible to keep the output of the micropump constant under normal use. As may be seen from the diagram of FIG. 8, the output 0 of a conventional two-valve micropump is a linear function of the pressure p prevailing at the outlet of the micropump (curve A). In contrast, the output 0 of a micropump of the invention is substantially constant in the normal operating pressure range (curve B). This is because, for a pressure below the maximum operating pressure, the variation in volume caused by displacement of the flexible wall is limited. The output is thus virtually the same as that corresponding to the maximum operating pressure.

What is claimed is:

1. A micropump comprising a plurality of wafers sealed to one another so as to form a pumping chamber defined by two bonded wafers defining a cavity formed by etching at least one of said bonded wafers, at least one inlet valve and at lest one outlet valve enabling the pumping chamber to communicate with one inlet channel and one outlet channel respectively, said micropump also comprising a control element arranged to resiliently displace a part of one of said bonded wafers constituting a flexible wall of the pumping chamber between a first position in which said flexible wall is relatively far from an opposing wall of the pumping chamber when said control element is not active and a second position in which said flexible wall is closer to said opposing wall when said control element is active, the displacements of said flexible wall causing suction of a fluid into the pumping chamber or the delivery thereof, and said pumping chamber comprising a stop means which defines said second position of said flexible wall.

2. A micropump according to claim 1 wherein the stop means comprises a projection formed on an inner face of the pumping chamber.

3. A micropump according to claim 2 wherein the surface of a stop means comes into contact with an inner face of the pumping chamber when the flexible wall assumes the second position, and is substantially planar.

4. A micropump according to claim 2 wherein the projection is formed in the bottom of the cavity during the etching thereof.

5. A micropump according to claim 1 wherein the stop means comprises the inner face of the wall of the pumping chamber located facing the flexible wall.

6. A micropump according to claim 1 wherein one of the wafers defining the pumping chamber is of silicon and the other of glass, the cavity being formed by etching the silicon wafer.

7. A micropump according to claim 6 wherein the flexible wall is one part of the silicon wafer.

8. A micropump according to claim 6 wherein the silicon wafer is of monocrystalline silicon.

9. A micropump according to claim 1 wherein said inlet valve is disposed in the wall of the pumping chamber opposite the flexible wall and wherein the stop comprises at least one part of this valve.

10. A micropump according to claim 1 wherein the control element comprises a piezoelectric disc fixed to the flexible wall.

11. A micropump according to claim 1 wherein the stop means comprises at least one part of the inner face of the flexible wall.

12. A micropump according to claim 3 wherein the projection is formed in the bottom of the cavity during the etching thereof.

13. A micropump according to claim 3 wherein one of the wafers defining the pumping chamber is of silicon and the other of glass, the cavity and the stop means being formed by etching the silicon wafer.

14. A micropump according to claim 4 wherein one of the wafers defining the pumping chamber is of silicon and the other of glass, the cavity and the stop means being formed by etching the silicon wafer.

15. A micropump according to claim 6 wherein the flexible wall is one part of the glass wafer.

16. A micropump according to claim 15 wherein the control element comprises a piezoelectric disc fixed to the flexible wall.

17. A micropump according to claim 7 wherein the control element comprises a piezoelectric disc fixed to the flexible wall.

18. A micropump according to claim 15 wherein said inlet valve is disposed in the wall of the pumping chamber opposite the flexible wall and wherein the stop means comprises at least one part of this valve.

19. A micropump according to claim 6 comprising a silicon wafer bonded between two glass wafers, said silicon wafer being etched on opposite sides to form at least two cavities each having an inner face opposite to a corresponding one of said glass wafers.

20. A micropump according to claim 19 wherein the control element comprises a piezoelectric disc fixed to the flexible wall.

21. A micropump according to claim 1 wherein a surface of the stop means comes into contact with an inner face of the pumping chamber when the flexible wall assumes the second position, and is substantially planar.

* * * * *

UNITED STATES PATENT AND TRADEMARK OFFICE
CERTIFICATE OF CORRECTION

PATENT NO. : 5,085,562
DATED : February 4, 1992
INVENTOR(S) : Harald van Lintel It is certified that error appears in the above-identified patent and that said Letters Patent is hereby corrected as shown below:

Column 6, line 59, change "lest" to --least--.

Signed and Sealed this

Twenty-seventh Day of April, 1993

*Attest:*

MICHAEL K. KIRK

*Attesting Officer*      *Acting Commissioner of Patents and Trademarks*